United States Patent [19]

Chase et al.

[11] Patent Number: 5,476,965
[45] Date of Patent: Dec. 19, 1995

[54] ENZYMATIC RESOLUTION OF SUBSTITUTED 2-METHYL-PROPIONIC ACID

[75] Inventors: Matthew W. Chase, Belmont, Calif.; Charles T. Goodhue, Rochester, N.Y.; Robert Seemayer; Gregory M. Whited, both of Belmont, Calif.

[73] Assignee: Genencor International, Inc., Rochester, N.Y.

[21] Appl. No.: 199,373

[22] Filed: Feb. 18, 1994

[51] Int. Cl.⁶ ........................................ C07B 55/00
[52] U.S. Cl. ..................... 562/401; 560/61; 560/102; 560/105
[58] Field of Search ..................... 562/401; 560/61, 560/102, 105

[56] References Cited

PUBLICATIONS

CA 112 (15):137568s 1989.
CA 115 (17):182683y 1991.
CA 120 (2):22822t 1993.
CA 118 (25):254492x 1993.

Primary Examiner—Paul J. Killos
Attorney, Agent, or Firm—Margaret A. Horn

[57] ABSTRACT

Provided are enzymatic methods for the selective hydrolytic resolution of certain enantiomers of a pharmaceutical compound, the pharmaceutical compound comprising a (±) mixture of a α-substituted 2-methyl proprionic acid derivative. Specifically provided is the selective enzymatic resolution of either the R(+) or S(−) enantiomer of (±)-ethyl ciprofibrate. Also provided are substantially pure enantiomers of R(+) and S(−) ciprofibrate.

14 Claims, No Drawings

ENZYMATIC RESOLUTION OF SUBSTITUTED 2-METHYL-PROPIONIC ACID

FIELD OF THE INVENTION

This invention relates to the enzymatic hydrolysis of substituted 2-methyl-propionic acid derivatives, particularly fibrate-related compounds. More specifically, this invention relates to certain enzymatic resolutions which selectively yield either the S(−) or the R(+) enantiomer of (±)-ethyl ciprofibrate, depending on the enzyme selected and its enantioselectivity.

BACKGROUND OF THE INVENTION

Fibrate-related compounds area class of compounds sharing a α-methyl-propionic acid locus as part of the overall fibrate structure. Fibrate-related compounds are known as lipid and/or cholesterol reducing agents and include, for example, gemfibrozil (Lopid, commercially available from Parke-Davis, U.S. Pat. Nos. 3,674,836 and 4,126,627), nafenopin, which has been studied by Ciba-Geigy for similar uses, and ciprofibrate (Ciprol or Lipanor available from Sterling, Winthrop, Inc., U.S. Pat. No. 3,948,973). The structures of these compounds are provided below:

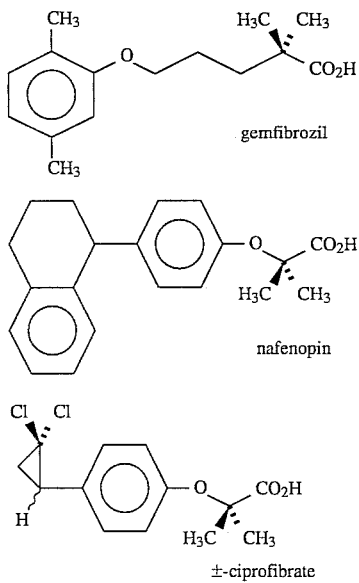

The compound ciprofibrate (α-2-methyl propionic acid) is currently being developed as a lipid reducing agent by Sterling Winthrop, Inc. The compound is produced as a (±)-racemate. It is known that the active enantiomer is the R(+) acid. Because the compound is a racemic mixture, commercial scale-up yields for the desired R(+)-enantiomer are low, additionally, the inactive S(−) compound may be associated with unwanted side effects. Therefore, it would be desirable to have a cost-effective high yield process for the selective production of one or more of the enantiomers as compared to the racemic mixture currently produced. There is a need for an enzymatic resolution process to selectively produce either the S(−) or the R(+) enantiomer of the free acid.

SUMMARY OF THE INVENTION

There are provided, processes for the selective resolution of either the S or R enantiomer of a racemic mixture of a substituted 2-methyl-propionic acid derivative, the process comprising reacting the propionic acid derivative with an appropriate enzyme under suitable conditions to yield substantially pure enantiomers of the starting compound, and optionally converting the enantiomer into the active form. In an embodiment of the present invention the proprionic acid derivative has the formula:

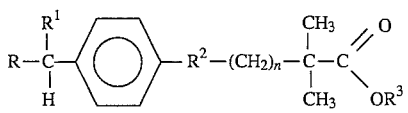

wherein:

R and $R^1$ defined individually are substituted or unsubstituted alkyl of C1–C4 (where the alkyl group can be substituted with halogen, sulfur or nitrile) or R and $R^1$ taken together with the asymmetric center of the proprionic acid derivative of Formula I form a substituted or unsubstituted 3–6 carbon member ring structure (where the ring structure can be substituted with halogen, alkyl of C1–C6 or aryl); provided, however, that R and $R^1$ differ in size by at least one carbon atom or equivalent bond length;

n is 0–6;

$R^2$ is O or $CH_2$, provided that $R^2$ can be on either side of the $(CH_2)_n$ chain; and $R^3$ can be any moiety subject to hydrolysis, for example, H, $NHR^4$ (where $R^4$ is H, alkyl or an amino acid), alkyl of 1–6 carbon atoms and substituted alkyl (where the substituent(s) can be halogen or CN).

Preferably the propionic acid derivative used in the present invention is a compound of Formula I wherein:

R and $R^1$ taken together with the asymmetric center form a 3-member substituted cyclic ring structure (where the substituent is a halogen);

$R^2$ is O; and n is 0.

Preferably the propionic acid derivative to be selectively resolved by the present invention is a chiral compound such as nafenopin or ciprofibrate and derivatives thereof.

A preferred embodiment of the present invention comprises the selective resolution of either the S(−) or R(+) enantiomer of (±)-ethyl ciprofibrate.

DETAILED DESCRIPTION OF THE INVENTION

Enzymatic hydrolysis reactions for resolution of active compounds are known in the art. However, surprisingly, we have found that enzymatic resolution of a group of compounds which are 2-methyl-proprionic acid derivatives (preferably chiral derivatives), with specific types of enzymes and/or with enzymes having different E values, will favor one enantiomer over the other. This finding is surprising, particularly with regard to ciprofibrate, because the distance between the side chain on the compound to be hydrolyzed and the asymmetric center of the molecule is so great (approximately 8 carbon atoms). Most successful enzymatic resolutions are done with compounds whose asymmetric center is only 1 or 2 atoms from the reaction center. In the present invention the distance between the side chain to be hydrolyzed and the asymmetric carbon center can be up to 8 carbon atoms (or equivalent bond lengths) apart.

As used herein the selectivity of an enzyme is referred to by its "E" value, which is measured by the equation of Chen, C.S., et al., J. Am. Chem. Soc. 1982 104:7294–7299, and provided below:

$$E = (K_{cat}/K_m)_{R\ enantiomer} / (K_{cat}/K_m)_{S\ enantiomer}$$

As used herein the optical purity of a resulting compound is referred to as its ee value, which is measured by the following equation:

$$\% \ ee_R = \left( \frac{[R] - [S]}{[R] + [S]} \right) \times 100$$

where the concentration of R and S enantiomer is in molar concentration.

As used herein "substantially pure" R and S enantiomers means that each is substantially free of the other. Therefore, for example, a substantially pure R enantiomer has little or no contamination with the S enantiomer. Little or no contamination means generally less than about 20% and preferably less than about 10%.

Racemic compounds which contain a mixture of R and S enantiomers and are therefore not optically pure, can be problematic from a manufacturing perspective. Racemic compounds useful as pharmaceutical agents may be especially troublesome because the mixture may result in poorer biological activity (and, thus, require higher dosage). The therapeutic activity of a racemic compound is often associated with only one of the enantiomers of the compound (for example, therapeutic activity of (±)-ciprofibrate is associated solely with the R(+) enantiomer). Similarly, it has been surmised that unwanted side effects may be associated with the second enantiomer.

Although the following discussion relates primarily to the resolution of (±)-ethyl ciprofibrate, it is understood that the present invention is applicable to all fibrate-related compounds, particularly those which are 2-methyl propionic acid derivatives.

Scheme 1 below shows the enzymatic hydrolysis of a preferred compound, (±)-ethyl ciprofibrate, into the R(+) and S(−) enantiomers using an ester hydrolase at pH 7.0.

Scheme 1: Enzymatic Hydrolysis

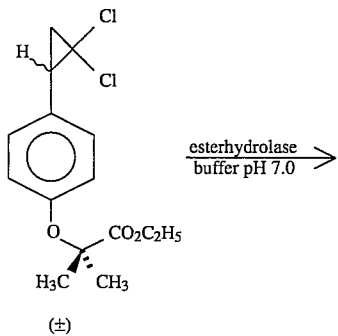

-continued
Scheme 1: Enzymatic Hydrolysis

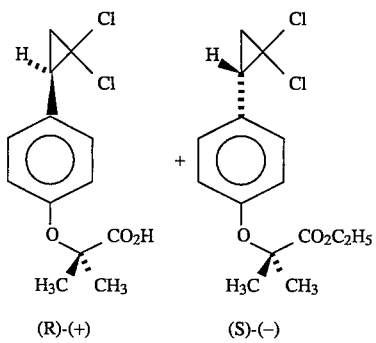

As seen in Scheme 1, the asymmetric center of the (±) compound is actually 8 carbon atoms away from the side Chain ($C_2H_5$) to be hydrolyzed. It should be understood that the term "carbon atoms" encompasses equivalent bond lengths and is used to define the distance between the asymmetric center and hydrolyzable side chain. Thus, the asymmetric center and the subject side chain may be 7 carbons and 1 oxygen away from each other. This is referred to as 8 equivalent bond lengths since oxygen-carbon and carbon-carbon bonds are similar in length.

Esterhydrolases, (esterases, lipases) and proteases available from various commercial sources were screened to determine their hydrolytic activity for the (±)-ethyl ciprofibrate substrate. The details of this screening process are set forth below. Generally, however, it was found that certain esterhydrolases showed enantioselectivity leading to the R(+) free acid in low yields with an optical purity of >40% ee. Preferred esterhydrolases are cholesterol esterases from microbial sources such as Candida and Pseudomonas, and lipases from microbial sources, particularly Candida.

Although this discussion primarily focuses on the desire to isolate selectively the R(+) enantiomer of ciprofibrate, which is the pharmaceutically active compound, it should be understood that compared to conventional chemical methods for preparing the active R(+) enantiomer of ciprofibrate it would be advantageous to first separate the enantiomers by enzymatic hydrolysis and then to subsequently recrystallize the free acid to yield the R(+) compound. The processes are exemplified below and it is contemplated that the enantioselective enzymatic resolution of the racemic ethyl ester and subsequent recrystallization will lead to improved yields and enhanced cost efficiency in the scale-up manufacture of the commercial product. It may also be advantageous to produce the S(−) isomer for pharmaceutical efficacy and toxicity studies.

While the esterhydrolases (esterases, lipases) are selectively hydrolysing the R-enantiomer of ethyl ciprofibrate (63%), we have found that proteases have reverse enantioselectivities. Thus, proteases are selective for the production of an R(+) ethyl ester/amide and the S(−) free acid. It is desirable to either obtain selectively the R(+) free acid directly or to isolate the R(+) ethyl ester/amide and to convert it to the free acid by saponification. Thus, for one aspect of this invention the selective resolution of (±)-ethyl ciprofibrate to obtain the R(+) free acid with an esterase is preferred, preferably using a cholesterol esterase. In another aspect of the present invention the selective hydrolysis of the S(−) ethyl ester or amide with a protease is preferred. The remaining R(+) ester or amide can be converted into the free acid. Such conversions can easily be achieved by techniques known to those skilled in the art, for example, saponification.

Proteases useful in the present invention may be from any source (microbial, mammalian, etc.). However, preferred proteases are Bacillus proteases (subtilisins).

It has also been found that in hydrolyses using enzymes with low selectivity (E value of less than about 15), the R(+) enantiomer is contaminated with the S(−) acid. In this case, it is contemplated that precipitation of the contaminated R(+)/S(−) mixture with a chiral amine will favor the R(+) crystallization.

Because of the reverse enantioselectivity of proteases as compared to lipases, one can achieve a high optical purity with either desired enantiomer (R(+) or S(−)).

Although the work exemplified below is limited to work with the ester (±)-ethyl ciprofibrate, it is contemplated that similar results could be achieved with other fibrate-related compounds including, for example, nafenopin.

EXPERIMENTAL

EXAMPLE 1

Screening for Suitable Lipases and Esterases 5 mg of (±)-ethyl ciprofibrate were incubated with 50 mg of enzyme in 1 ml phosphate buffer, pH 7.0, at 30° C. After 6 hours 1 ml of a chloroform-methanol 1–4 mixture was added and the solution was extracted with 2 ml ethyl acetate to isolate the product. The organic phase was evaporated and analyzed for the free acid via HPLC using a chiral cyclodextrine column. Using this method, 52 enzyme preparations were screened. The results are summarized in Tables 1 and 2. Table 1 shows only those esterhydrolases which showed hydrolytic activity.

HPLC Conditions:

Column: CYCLOBOND I β-SN (250×4.6 mm); commercially available from Astec.
Mobile Phase: $CH_3CN$-$CH_3OH$ 95-5.
Modifier: triethylamine 0.4 ml/l acidic acid 0.5 ml/l
Flow: 1 ml/min
Detection: UV 236 nm

TABLE 1

Esterhydrolases Screened

| Enzyme | Source | Commercial Supplier | Optical Purity of Obtained Acid (ee) |
|---|---|---|---|
| Cholesterol esterase | Candida rugosa | Genzyme | 21% |
| Cholesterol esterase | microbial | Genzyme | 25% |
| Cholesterol esterase Grade II | Candida rugosa | Genzyme | 29% |
| Cholesterol esterase | Porcine pancreas | Calzyme | <5% |
| Cholesterol esterase N | microbial | Finn-sugar | 37% |
| Cholesterol esterase Type A | microbial | Toyobo | 41% |
| Cholesterol esterase | microbial | Nagase | 45% |
| Cholesterol esterase | Pseudomonas | Amano | 49% |
| Cholesterol esterase | microbial | Calbiochem | 53% |
| Cholesterol esterase N | microbial | Toyo Jozo | 57% |
| Cholesterol esterase | Bovine pancreas | Sigma | <5% |
| Esterase | Porcine liver | Sigma | <5% |
| Lipase AY 30 | Candida cylindracea | Amano | 69% |
| Lipase Type VII | Candida cylindracea | Sigma | 73% |

Table 1 shows the 14 esterhydrolases which demonstrated hydrolytic activity for the substrate. Seven of the esterhydrolases shown in Table 1 (five esterases and two lipases) showed reasonable enantioselectivity leading to the free acid with an optical purity >40% ee. In all cases the produced acid had the desired (R)-(+)-configuration as confirmed by correlation with an authentic sample.

TABLE 2

Lipases Screened

| Microbial Source | Commercial Supplier |
|---|---|
| Chromobacterium viscosum | Toyo Jozo |
| Mucor javanicus | Amano M-AP 10 |
| Mucor miehei | Biocatalysts |
| Geotrichum candidum | Amano GC 5 |
| Rhizopus niveus | Amano N conc. |
| Penicillium roquefortii | Amano R 10 |
| Pseudomonas | Amano PL 105 |
| Penicillium cyclopium | Amano G |
| Rhizopus javanicus | Biocatalysts |
| Pseudomonas sp. | Amano SAM II |
| Aspergillus niger | Amano AP 6 |
| Rhizopus javanicus | Amano F-AP 15 |
| Humicola lanuginosa | Amano CE |
| Wheat germ | Sigma |

Table 2 shows the 14 lipase-enzyme preparations screened by the process of Example 1. The lipases listed in Table 2 showed no hydrolytic activity for the (±)-ethyl ciprofibrate.

EXAMPLE 2

Using the cholesterol esterase Grade II (available from Genzyme) shown in Table 1 to yield a 29% optically pure free acid, the following scale-up experiment was performed. 3.16 g (10 mmol) (±)-ethyl ciprofibrate was stirred in 20 ml 0.005M phosphate buffer, pH 7.0, in the presence of 200 mg of cholesterol esterase (available from Genzyme). In order to perform the enzymatic hydrolysis without significant drop in the pH value, the reaction was carried out under pH-stat conditions. A 1M sodium hydroxide solution was added by an autotitrator during the reaction to neutralize the formed carboxylic acid. The reaction was monitored via the consumption of the sodium hydroxide solution which directly reflects the conversion. The reaction stopped after 5 days with an approximately 27% conversion rate indicating the possibility of a product inhibition. The aqueous phase was acidified with 1M hydrochloric acid and extracted three times with 50 ml ethyl acetate each. The unified organic phases were dried over sodium sulfate and the solvent was evaporated. The crude mixture was separated via column chromatography on silica gel (hexane-diethyl ether 1-1).

Yields: 710 mg (2.46 mmol) (R)-ciprofibratic acid, 25% of theory colorless solid 2.00 g (6.30 mmol) (S)-ethyl ciprofibrate, 63% of theory colorless liquid A schematic of the reaction is provided below as Scheme 2, which also shows the additional steps described in Example 3 below.

Scheme 2: Enzymatic Resolution with Cholesterol Esterase (±)-ethyl ester $\xrightarrow{\text{cholesterol esterase}}_{\text{buffer pH 7.0}}$ -continued
Scheme 2: Enzymatic Resolution with Cholesterol Esterase

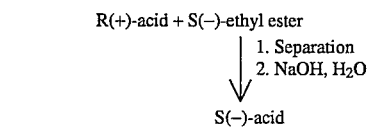

EXAMPLE 3

Saponification of the (S)-Ethyl Ciprofibrate 200 mg of the S(−)-ethyl ester from Example 2 were stirred with 10 ml distilled water:and 200 mg sodium hydroxide for hours at room temperature. The solution was acidified and extracted three times with ethyl acetate. The organic phases were unified, dried over sodium sulfate and the solvent evaporated.

Yield: 160 mg (0.55 mmol) (S)-ciprofibratic acid, 88% of theory colorless liquid, crystallizes upon standing at room temperature The optical purities of the two obtained acid fractions R(+) free acid from Example 2 and S(−) free acid from Example 3 were determined via chiral HPLC analysis. The data were used to calculate the enantioselectivity of the reaction using well established equations (see C. S. Chen, Y. Fujimoto, G. Girdaukas and C. J. Sih, J. Am. Chem. Soc. 1982, 104:7294–7299; an excellent review is given by C. J. Sih and S. H. Wu, "Resolution via Biocatalysis" in Topics of Stereochemistry, 1989, Vol. 19, 63–125). Results are shown below in Table 3.

TABLE 3

| Calculated Kinetic Parameter | Optical Purities |
| --- | --- |
| E = 15.4 | Acid: 83.7% ee |
| c = 27.8% | Ester: 32.2% ee |
| E: selectivity coefficient | c: conversion |

EXAMPLE 4

Screening of Proteases

Selected proteases were screened for their hydrolytic activity toward the hydrolysis of (±)-ethyl ciprofibrate. The following screening method was used and the results of the screening are summarized in Table 4.

317 mg (1.0 mmol) (±)-ethyl ciprofibrate were stirred with 10 ml buffer, pH 8.0, and 100 mg of the desired protease. After 1 day 500 μl samples were taken, 2 drops of 1M hydrochloric acid were added and the aqueous phase were extracted with 500 μl ethyl acetate. The obtained organic phase were directly used to determine the rate of hydrolysis using HPLC.

HPLC Conditions:

Column: RP-18 (250×4.6 mm) 5 μm
Mobile Phase: Methanol-water 80–20
Modifier: Acidic acid 0.6 ml/l
Flow: 1 ml/min
Detection: UV 254 nm

TABLE 4

Hydrolysis of (±)-Ethyl Ciprofibrate Using Various Proteases

| Microbial Source or Enzyme | Supplier | Hydrolysis | E Value |
| --- | --- | --- | --- |
| Crude Papain | Sigma | No | |
| Aspergillus sojae | Sigma Typ XIX | No | |
| Rhizopus sp. | Sigma Typ XVIII | No | |
| Bovine Pancreas | Sigma Typ I | No | |
| α-Chymotrypsin | Sigma | No | |
| Streptomyces griseus | Sigma Typ XIV | No | |
| Bacillus protease | Amgen[1] | Yes | 10 |
| Subtilisin Carlsberg | Sigma | Yes | 7 |
| Protease 899 | GCI | Yes | 16 |
| Bacillus lentus subtilisin | GCI[2] | No | |
| Savinase | Novo Nordisk | Yes | 2 |
| Proteinase K | Int. Biotechnologies | Yes | 11 |

[1]See U.S. Pat. No. 4,814,931 (incorporated herein by reference)
[2]See U.S. Pat. No. 5,185,258 (incorporated herein by reference)

Based on the results shown in Table 4, certain of the proteases, particularly Protease 899 appears to be a good candidate for this process.

EXAMPLE 5

Improvement of Optical Purity by Recrystallization 110 mg of (R)-(+)-ciprofibrate (74% ee) are recrystallized from 1.6 ml n-hexane and 0.2 ml toluene. After cooling the mixture to room temperature the precipitated acid is recovered by filtration.

Yield: 60 mg colorless crystalline compound, 85% ee

What is claimed is:

1. A process for the enzymatic resolution of one or more enantiomers of a proprionic acid derivative of the formula:

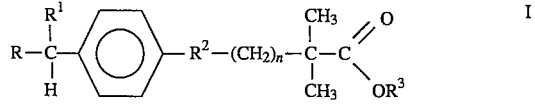

wherein:

R and $R^1$ defined individually are substituted or unsubstituted alkyl of C1–C4 (where the alkyl group can be substituted with halogen, sulfur or nitrile) or R and $R^1$ taken together with the asymmetric center of the compound of Formula I form a substituted or unsubstituted cyclic ring structure of C3–C6 (wherein the ring structure may be substituted with alkyl of C1–C6, halogen or aryl); provided, however, that either R or $R^1$ is larger than the other by at least one carbon atom or equivalent bond length;

n=0–6;

$R^2$ is O or $CH_2$ provided that $R^2$ can be on either side of the $(CH_2)_n$ chain; and $R^3$ is H, $NHR^4$ (where $R^4$ is H, alkyl or an amino acid), alkyl of 1–6 carbon atoms or substituted alkyl of 1–6 carbon atoms (where the substitutent is selected from the group consisting of halogen and CN);

the process comprising reacting the proprionic acid derivative with an esterhydrolase or protease to selectively resolve the substantially pure R or S enantiomer under conditions suitable for such resolution.

2. A process of claim 1 wherein R and $R^1$ are independently $CH_2Cl$ and $C_2H_4Cl$.

3. A process of claim 1 wherein R and $R^1$ taken together with the asymmetric center of the compound of Formula I form a 3-member substituted cyclic ring structure.

4. A process of claim 3 wherein the 3-member ring structure is substituted with halogen.

5. A process of claim 1 wherein $R^2$ is O.

6. A process of claim 1 wherein n=0.

7. A process of claim 1 wherein $R^3$ is alkyl of 1–6 carbon atoms or halogenated alkyl of 1–6 carbon atoms.

8. A process of claim 1 wherein R and $R'''$ taken together form a di-chloro substituted 3-member cyclic ring; $R^2$=O; and n=0.

9. A process of claim 1 wherein the propionic acid derivative is (±)-ethyl ciprofibrate.

10. A process of claim 9 comprising contacting (±)-ethyl ciprofibrate with an appropriate esterhydrolase to yield the R(+) free acid of ciprofibrate with an optical purity of about >40% ee.

11. A process of claim 10 wherein the esterhydrolase is a cholesterol esterase or a lipase.

12. A process of claim 11 wherein the cholesterol esterase is from a microbial source and the lipase is from a Candida organism.

13. A process of claim 12 wherein the lipase is from *Candida cylindracea*.

14. A process of claim 9 comprising contacting (±) ethyl ciprofibrate with an appropriate protease to yield the S(−) free acid of ciprofibrate with an optical purity of about 40% ee.

* * * * *